United States Patent [19]

Sweetman et al.

[11] Patent Number: 5,682,145
[45] Date of Patent: Oct. 28, 1997

[54] TOXIC GAS DETECTOR WITH A TIME MEASUREMENT SENSOR

[75] Inventors: Gerald Patrick Sweetman, Colorado Springs; Gary Ross Mitchell, Boulder; Marcus Leroy Caldwell, Colorado Springs; William Louis Witt, Broomfield, all of Colo.

[73] Assignee: Sensor Tech Incorporated, Sioux Falls, S. Dak.

[21] Appl. No.: 497,943

[22] Filed: Jun. 30, 1995

[51] Int. Cl.$^6$ ..................................................... G08B 17/10
[52] U.S. Cl. .......................... 340/632; 73/23.2; 73/31.05
[58] Field of Search ................................. 340/632, 633, 340/634; 73/23.2, 23.31, 31.05

[56] References Cited

U.S. PATENT DOCUMENTS

| | | | |
|---|---|---|---|
| 4,231,249 | 11/1980 | Zuckerman | 340/632 |
| 4,338,526 | 7/1982 | Martin et al. | 340/632 |
| 4,464,651 | 8/1984 | Duhame | 340/634 |
| 4,860,223 | 8/1989 | Grilk | 340/632 |
| 5,049,861 | 9/1991 | Grace et al. | 340/632 |
| 5,066,466 | 11/1991 | Holter et al. | 422/98 |
| 5,252,949 | 10/1993 | Kirby et al. | 340/632 |
| 5,264,833 | 11/1993 | Jeffers et al. | 340/632 |
| 5,276,434 | 1/1994 | Brooks et al. | 340/632 |
| 5,280,273 | 1/1994 | Goldstein | 340/632 |
| 5,331,310 | 7/1994 | Stetter et al. | 340/632 |
| 5,402,665 | 4/1995 | Hart et al. | 340/632 |

*Primary Examiner*—Jeffery Hofsass
*Assistant Examiner*—Edward Lefkowitz
*Attorney, Agent, or Firm*—Brenda Speer

[57] ABSTRACT

The present invention is a carbon monoxide or other toxic gas detector. The detector of the present invention detects the presence of carbon monoxide in an air sample by measuring the time required for the sensor circuitry to charge. Such a measurement technique eliminates the inaccuracies inherent in prior art detectors which measure the resistance of the sensor circuitry upon exposure to carbon monoxide. The detector of the present invention is controlled by a microprocessor which enables the detector to retain in memory air sample readings of carbon monoxide or other toxic gas. If the detector registers four consecutive readings which indicate the presence of carbon monoxide in an air sample in a concentration greater than or equal to about 100 ppm, then the alarm of the detector will be triggered, thereby alerting the user to a dangerous concentration of carbon monoxide gas in the air. Such a detection cycle enables the detector to detect not only high level, lethal concentrations of carbon monoxide in the air, but also, chronic, low level harmful concentrations of carbon monoxide in the air.

26 Claims, 10 Drawing Sheets

TOXIC GAS DETECTOR WITH A TIME MEASUREMENT SENSOR

FIELD OF THE INVENTION

The invention relates to a toxic gas detector and, more particularly, to a carbon monoxide detector, wherein the toxic gas detector measures a circuitry charge time for a sensor to detect the presence of a toxic gas, such as carbon monoxide, in an air sampling.

BACKGROUND OF THE INVENTION

The public awareness of the hazards of dangerous concentrations of carbon monoxide or other toxic gas in the air has greatly increased in recent years. As has been known for some time, lethal concentrations of carbon monoxide can impair a person very quickly, with death following shortly thereafter. But also, as recent studies have shown, long term exposure to low levels of carbon monoxide can also impair a person, make him ill, and cause physiological damage to his body. The symptoms of carbon monoxide exposure are similar to those of influenza and include nausea and headache. At high concentration levels, carbon monoxide quickly physically incapacitates a person, although he would remain mentally alert. After physical incapacity sets in, the exposed person has about 20 minutes to live if he remains in the presence of carbon monoxide.

Accordingly, there is a need for detectors which can detect the presence of carbon monoxide or other toxic gas in the air of residences, automobiles and work places. Once a toxic gas is detected, the occupant of a residence, automobile or work place can be alerted to the danger by a toxic gas detector and vacate the premises. Then the problem can be corrected in order to avoid future exposure, and its attendant ill effects, to carbon monoxide or other toxic gas.

Carbon monoxide or other toxic gas detectors are known. The prior art detectors detect the presence of carbon monoxide or other toxic gas in the air by measuring the change in resistance in the gas sensor circuitry which occurs when the sensor is exposed to a toxic gas.

Examples of such prior art detectors which measure a change in resistance of a gas sensor circuitry in the presence of carbon monoxide or other toxic gas are U.S. Pat. No. 5,066,466 by Hölter et al. for an "Apparatus for Indicating the Presence of Toxic Substances in Air that is Supplied to a Personnel-Occupied Space", issued Nov. 19, 1991; U.S. Pat. No. 5,252,949 by Kirby et al. for a "Chemical Sensor for Carbon Monoxide Detection", issued Oct. 12, 1993; U.S. Pat. No. 5,264,833 by Jeffers et al. for an "Automatic Leak Detector", issued Nov. 23, 1993; U.S. Pat. No. 5,276,434 by Brooks et al. for a "Carbon Monoxide Concentration Indicator and Alarm", issued Jan. 4, 1994; and U.S. Pat. No. 5,331,310 by Stetter et al. for an "Amperometric Carbon Monoxide Sensor Module for Residential Alarms", issued Jul. 19, 1994. In operation, when the sensors of these prior art detectors are exposed to carbon monoxide or other toxic gas, the flow of electricity through the circuitry is enhanced, thus, decreasing the circuitry resistance. The decreased resistance in the circuitry indicates the presence of carbon monoxide or other toxic gas in the air and triggers an alarm of the detector to alert a user.

These prior art detectors all have the disadvantage of having a wide range of variation in the resistance value of the gas sensor circuitry from about 1,000 ohms to about 15,000 ohms. To compensate for the resistance range variation, the prior art detectors use a potentiometer in series in the sensor circuitry to compensate for an initial resistance value of the sensor. The potentiometers are manually adjusted by a person who reaches into a sealed carbon monoxide chamber through gloves which are integral with the chamber to adjust the potentiometer screw with a jeweler's screwdriver. These three highly sensitive variables, gloved hands, tiny potentiometer screws and the use of a jeweler's screwdriver, make it extremely difficult to calibrate the potentiometer so that it accurately compensates for the resistance value of the sensor.

Another prior art device is U.S. Pat. No. 5,280,273 by Goldstein for a "Toxic Gas Detector System Having Convenient Battery and Sensor Replacement", issued Jan. 18, 1994. Goldstein generally discloses a carbon monoxide detector which uses a biomimetric sensor which mimics the human response to various toxic gases and vapors. The sensor is a chemical which changes optical density in response to exposure to carbon monoxide. This detector measures the light transmission characteristics of the sensor in order to detect the presence of carbon monoxide. A disadvantage of this detector is that the sensor can be easily contaminated by contact with airborne particles, thus hampering the ability of the detector to detect the presence of a toxic gas, such as carbon monoxide, and creating a likelihood of false alarms created by any airborne particle, such as dust, which may trigger the detector alarm.

U.S. Pat. No. 5,049,861 by Grace et al. for "Method and System for Detecting Underground Mine Fires", issued Sep. 17, 1991, generally discloses a carbon monoxide based, diesel discriminating, fire detection system and method which significantly reduces the threshold of carbon monoxide needed to detect a fire in a mine that also contains carbon monoxide from diesel equipment. It is presumed that this system also uses a resistance measurement to detect the presence of carbon monoxide gas, because Grace et al. teach that the prior art electrochemical, semiconductor or catalytic sensors which do measure resistance, are suitable for use in their system. Here again, as previously discussed, this prior art system would also have the wide variations in resistance values for the sensor.

Accordingly, there is a need for a carbon monoxide or other toxic gas detector which eliminates the wide variations in sensor resistance values and the resulting need to make manual potentiometer adjustments, which are extremely susceptible to human error, and, therefore, are inherently inaccurate, to correct for such resistance value variations. Such manual adjustments are also labor intensive and, thus, the detectors are expensive to manufacture, because of high labor costs. There is also a need for a carbon monoxide detector which has the ability to detect the presence of carbon monoxide or other toxic gas at not only high concentration lethal levels, but also at chronic, low level concentration harmful levels. As will be better understood by the detailed invention description which follows, the carbon monoxide detector of the present invention overcomes these prior art detector disadvantages and also contributes highly desirable advantages to the art of carbon monoxide or other toxic gas detection.

SUMMARY OF THE INVENTION

The present invention is a gas detector comprising the elements of a gas sensor; a capacitor; a transformer; a gated time measuring device; and a permanent memory chip; all of which are interconnected by means of and are integral with a circuit board, wherein the gated time measuring device measures a time for the sensor to charge in the presence of a gas. The capacitor and sensor are in a series circuit with each other. The detector further comprises an audio alarm, a visual alarm and a casing for housing the detector elements.

In a preferred embodiment, the gated time measuring device is a microprocessor. The microprocessor will register an alarm state if a gas concentration in an air sample is greater than or equal to about a pre-determined concentration. The microprocessor will trigger and flash a visual alarm for each alarm state and further will trigger an audio alarm upon four consecutive alarm state registrations. The microprocessor will trigger an audio alarm and a visual alarm upon detection of a pre-determined gas concentration in an air sample. Preferably, the microprocessor makes a time measurement about every two and one half minutes.

Further attributes of the detector of the present invention is that the microprocessor is able to screen out transient hydrocarbon exposure events to the sensor. Also, preferably, the detector may be reset.

A gas which the detector may specifically detect for is carbon monoxide. If the gas is carbon monoxide, then the sensor is selected from the group consisting of a tin dioxide sensor and a copper manganese dioxide sensor.

DETAILED DESCRIPTION OF THE INVENTION

Figure 1B:
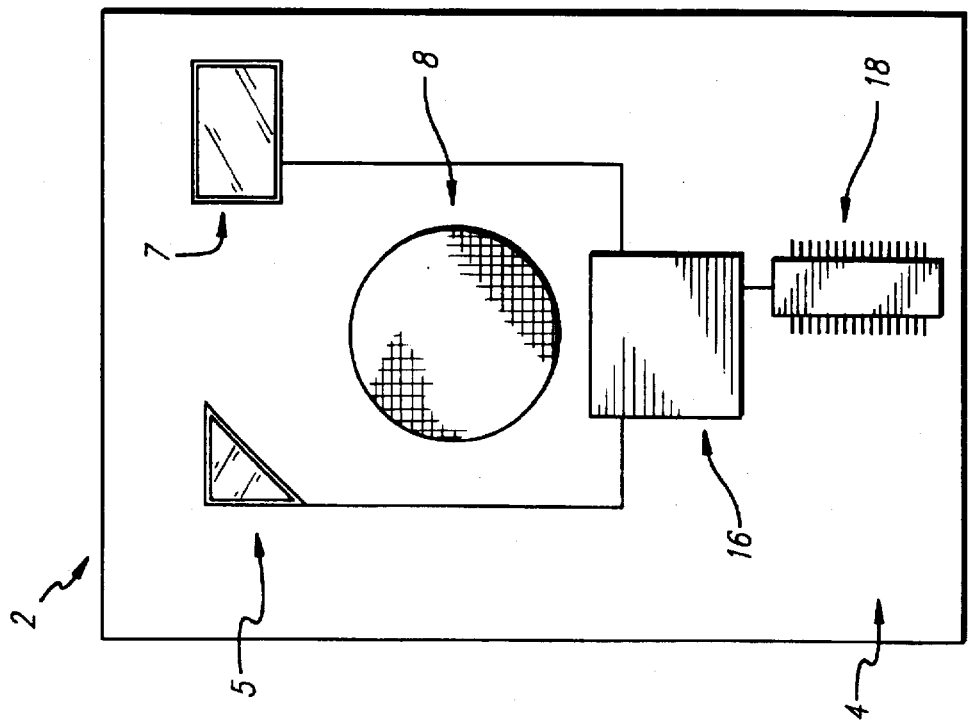
FIGS. 1A and 1B are front and back plan views, respectively, of the firmware of the detector of the present invention.

The detector of the present invention will be disclosed in its best mode with its preferred embodiment described. The preferred embodiment of the detector of the present invention is a carbon monoxide gas detector. As can be appreciated by those of ordinary skill in the art, the detector of the present invention can be readily adapted to detect other toxic gases by substituting a different sensor in the detector which is specifically sensitive to a particular toxic gas to be detected. However, even with such a substitution, the basic operational concept and circuitry of the detector of the present invention will remain essentially the same.

Pursuant to the current specifications of Underwriters Laboratories, Inc. (UL) (located in Chicago, Ill.), the detector of the present invention is known as a single user station detector, versus a multiple station detector. A unique feature of the detector of the present invention is its circuitry.

The prior art carbon monoxide detectors typically use a tin dioxide sensor in the detector to detect the presence of carbon monoxide. The prior art detectors measure the resistance in the sensor circuitry in order to determine if carbon monoxide is present in an air sample. Since the concentration of carbon monoxide in an air sample and the resistance of the sensor circuitry are inversely related, when a sensor is exposed to carbon monoxide, its resistance value decreases. Carbon monoxide in effect enhances the flow of electricity through the sensor circuitry.

A common sensor in use within the carbon monoxide detector industry is the Figaro brand tin dioxide sensor (manufactured by Figaro Engineering, Inc., Osaka, Japan, and distributed by Figaro USA, Inc., Wilmette, Ill., U.S.A.). The Figaro sensor is an unwieldy sensor to use, because the resistance value of each sensor is different. An initial resistance value for each sensor ranges from about 1,000 ohms to about 15,000 ohms; however, each sensor has a fixed resistance value within this range. The Figaro sensor also has the inverse relationship of carbon monoxide concentration to sensor resistance value as previously discussed.

To compensate for the range of resistance values for each sensor, the prior art detectors use a potentiometer to compensate for an initial resistance value of the sensor. Typically, prior to assembly of a sensor in parallel with a potentiometer, the sensors are initially sorted by resistance value. Then each sensor having a known resistance value is then put in a parallel circuit with a potentiometer and the potentiometer is calibrated so that the sensor can detect a known carbon monoxide concentration which corresponds to the sensor's resistance value. As previously discussed, the potentiometers are manually adjusted by a person who reaches into a sealed carbon monoxide chamber through gloves which are integral with the chamber to adjust the potentiometer screw with a jeweler's screwdriver. These three highly sensitive variables, gloved hands, tiny potentiometer screws and the use of a jeweler's screwdriver, make it extremely difficult to calibrate the potentiometer.

Figure 2B:
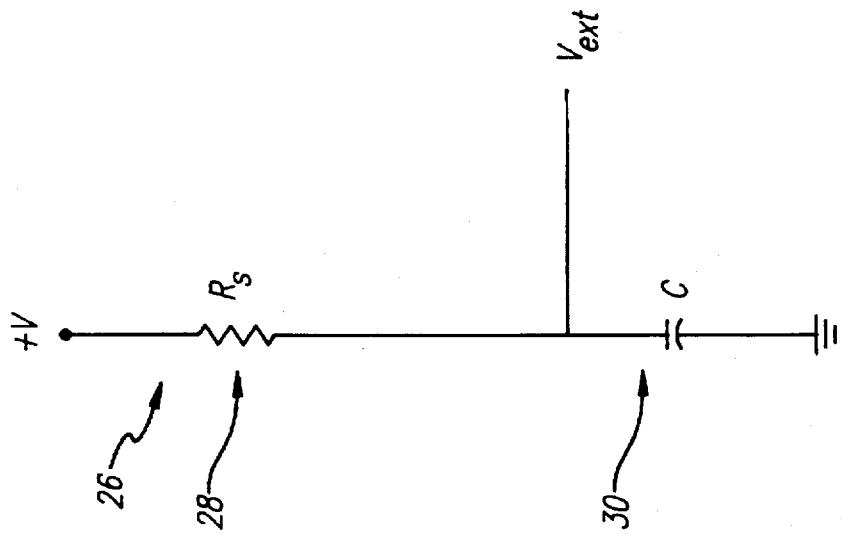
FIGS. 2A and 2B are schematics of the prior art sensor circuitry and that of the detector of the present invention, respectively.
Figure 2A:
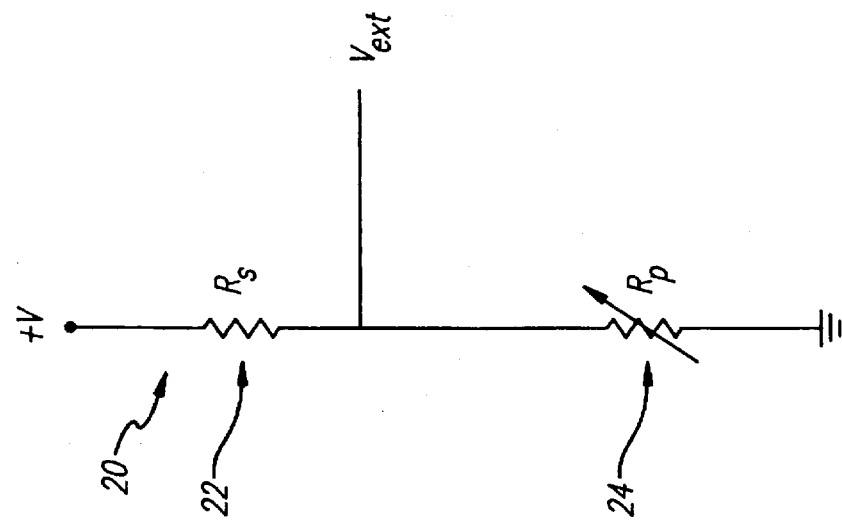
Figure 3A:
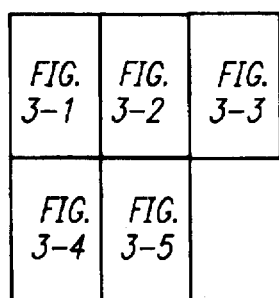
FIG. 3 is a flowchart for the firmware functions of the detector of the present invention.
Figures 1, 3:
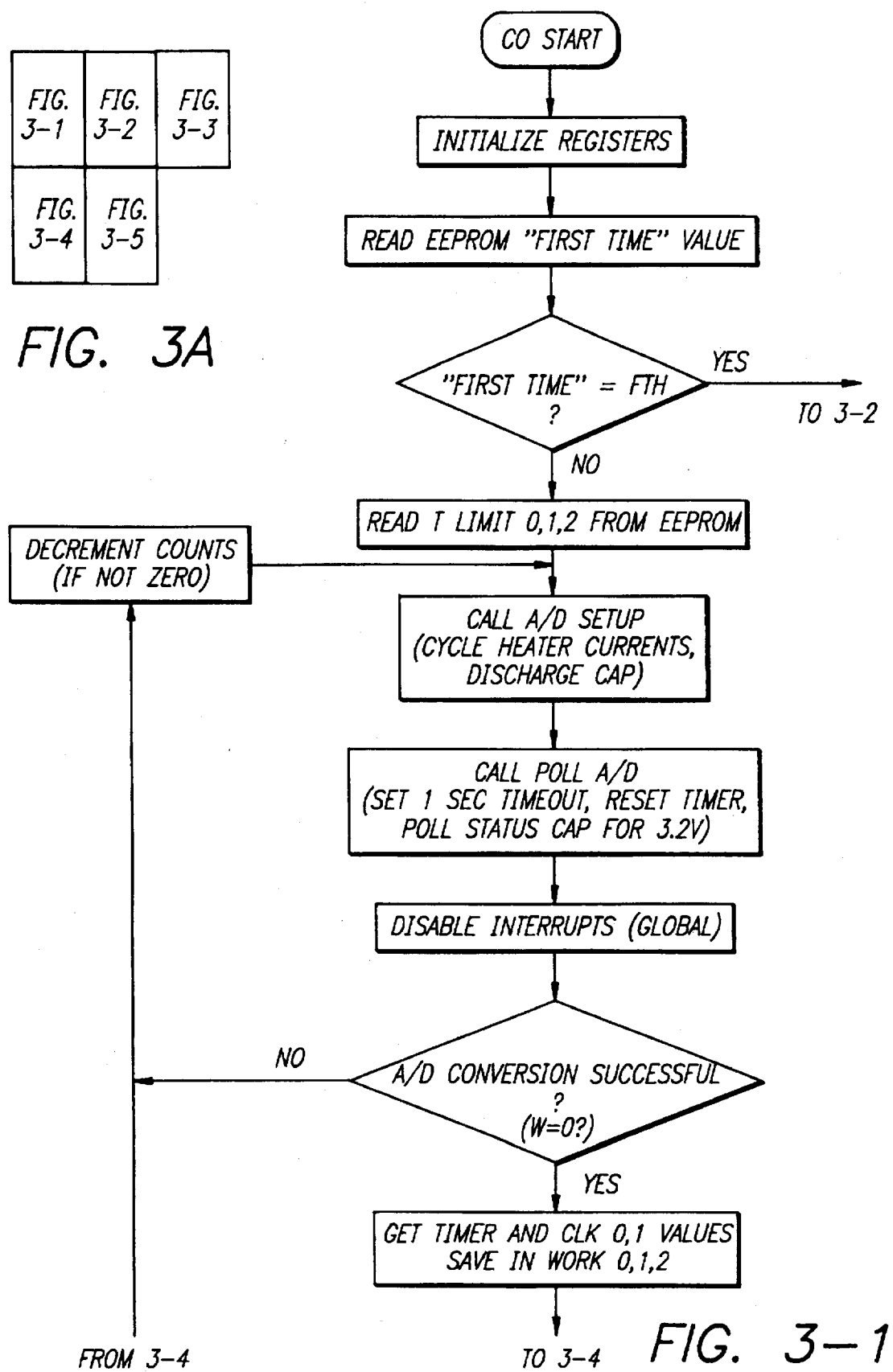
Figures 2, 3:
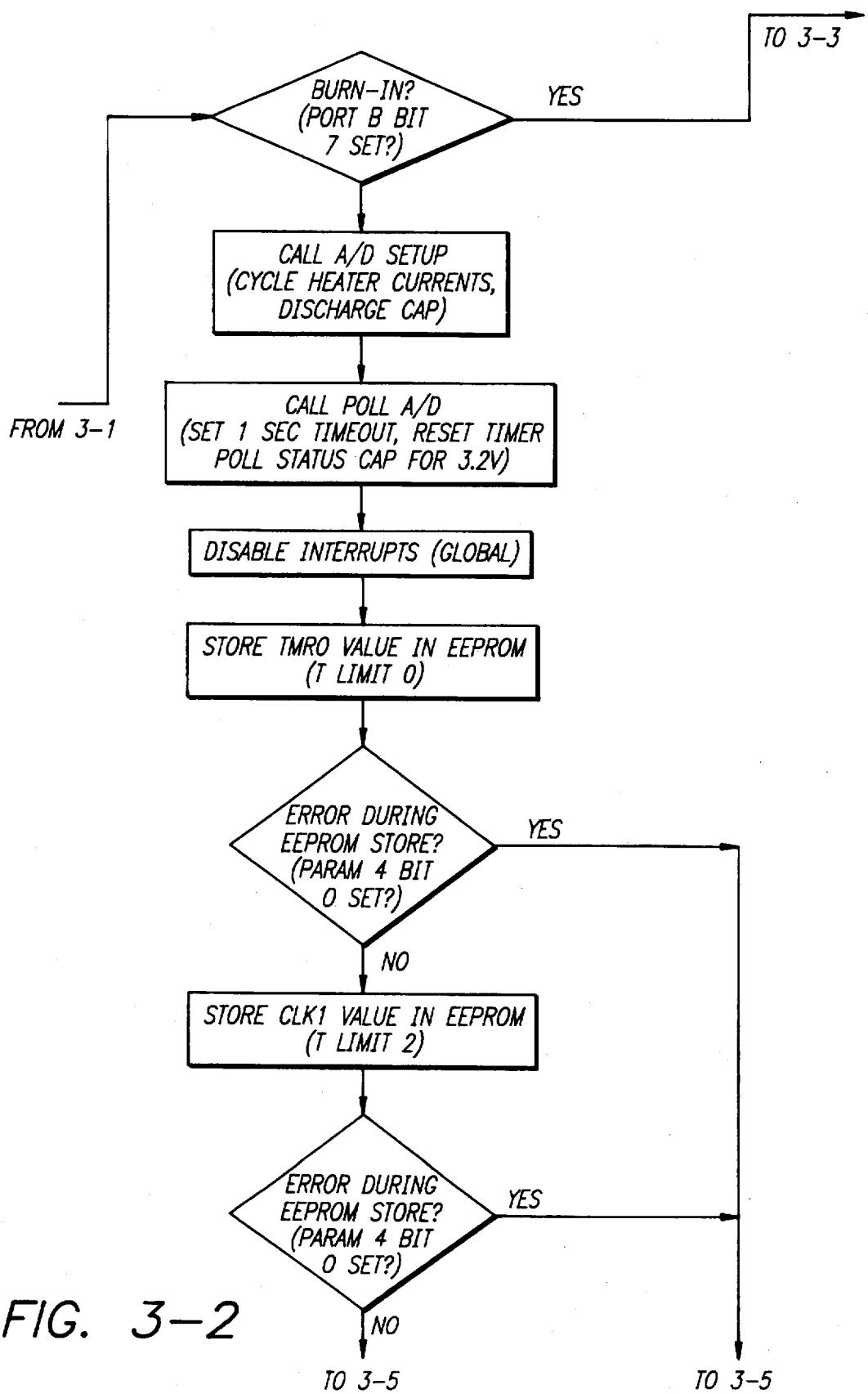
Figure 3:
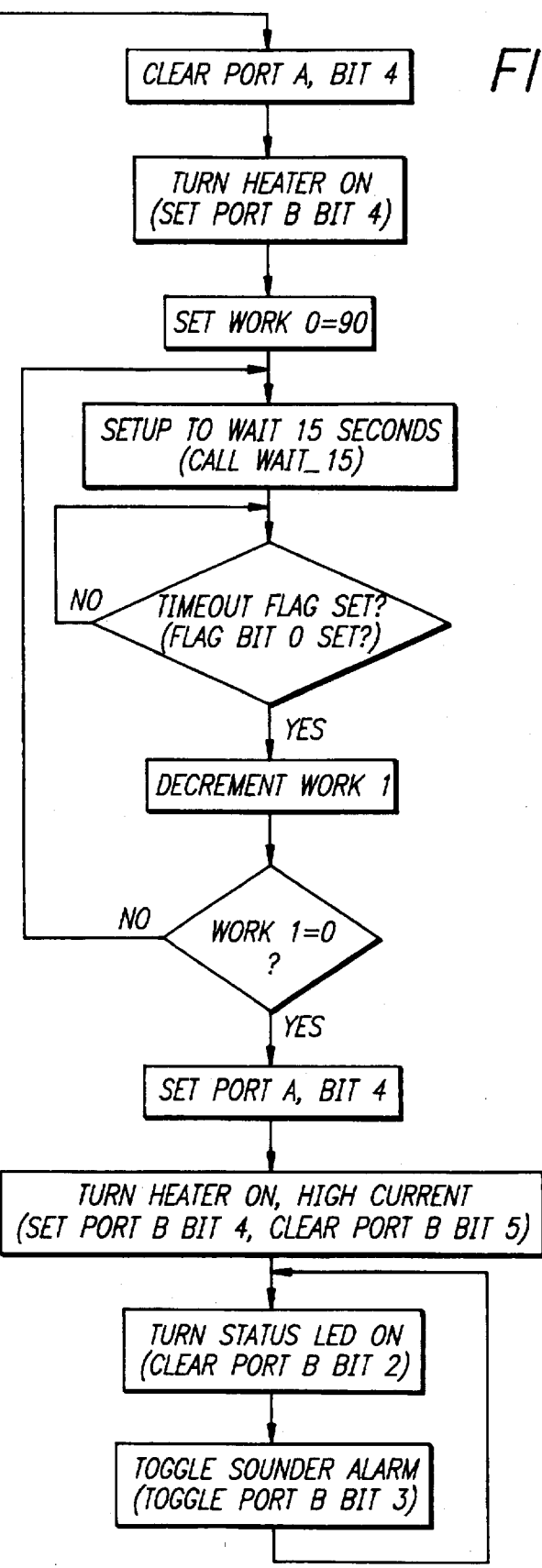
Figures 3, 4:
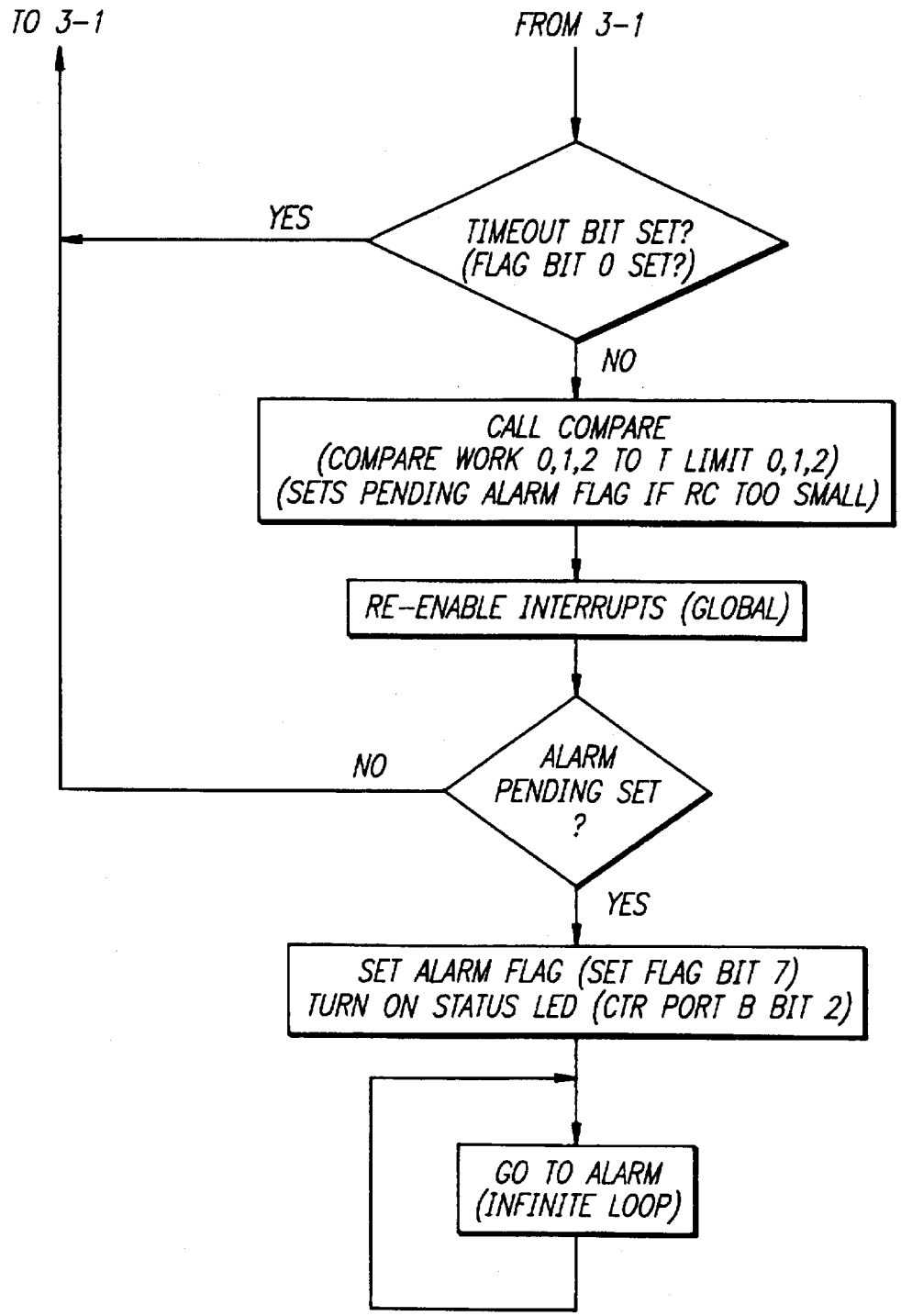
Figures 3, 4, 5:
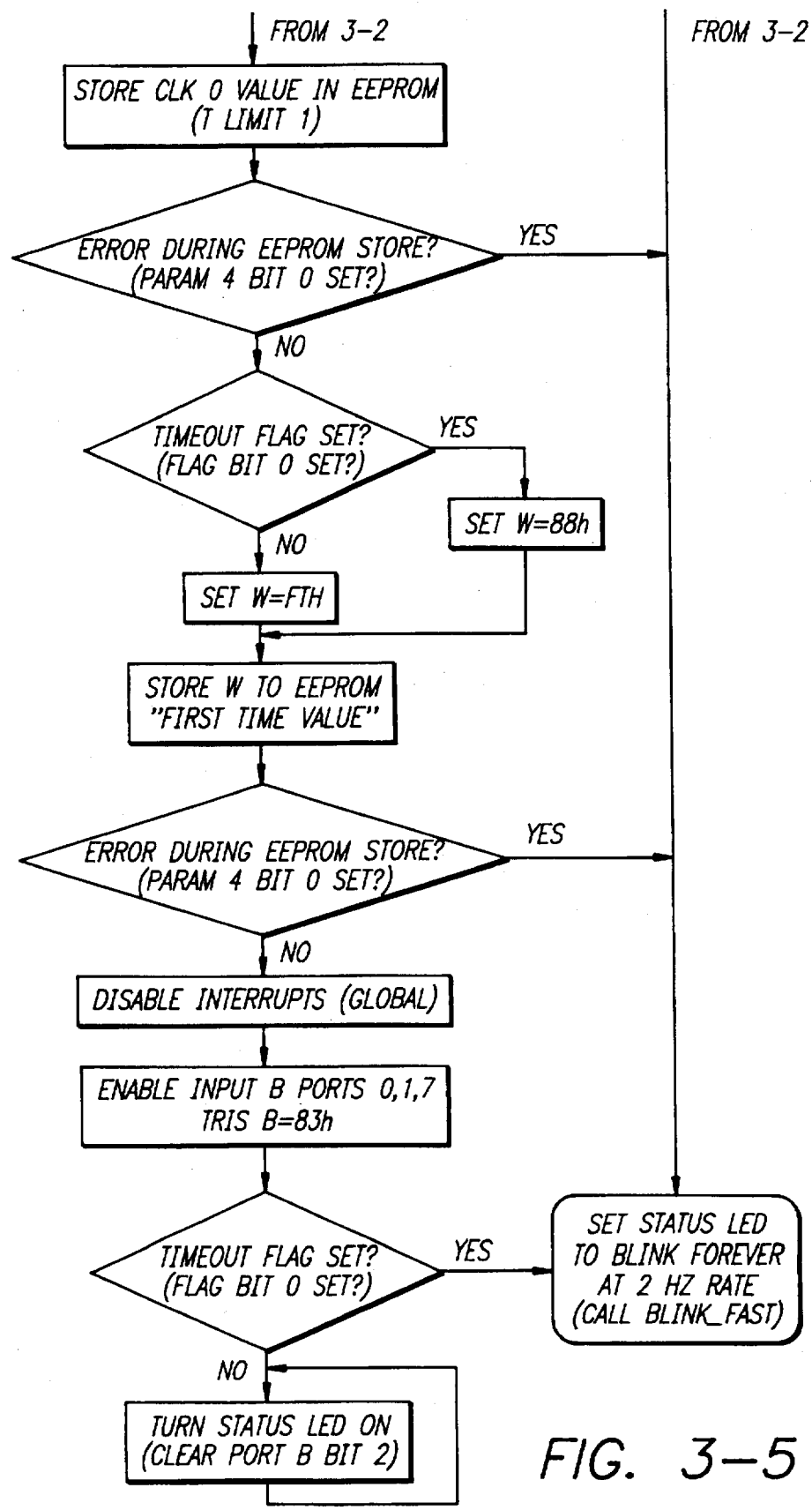

An example of the circuitry of the prior art detectors is shown in FIG. 2A. The circuit 20 consists of a sensor 22 having a resistance value of $R_s$ in series with a potentiometer 24 having a resistance value of $R_p$. Voltage (+V) is then passed through the circuit 20, which allows for the unknown resistance value of the sensor to be determined.

In stark contrast to the prior art detector circuitry is the circuitry of the detector of the present invention. In FIG. 2B, circuit 26 of the detector of the present invention is a sensor 28 having a resistance value of $R_s$ in series with a capacitor 30 having a capacitance value of C.

A resistor-capacitor series circuit enables the time required for the circuitry to fully charge to be measured versus measuring the resistance of the circuitry. This time measurement accurately compensates for the variance in the sensor's resistance value, whereas the resistance measurement done with the prior art circuitry with a potentiometer does not.

Since a capacitor is a reservoir of charge, time is required for the capacitor to fully charge and subsequently discharge its excess charge. In the presence of carbon monoxide, the resistance value of the sensor of the detector of the present invention is lowered, because carbon monoxide concentration and the sensor resistance are inversely related. Because the resistance of the sensor is lowered, the time required for the capacitor to charge and discharge its excess charge is also lowered. Accordingly, the time required for the detector circuitry to charge also decreases.

In the detector of the present invention, the voltage in the resistor-capacitor circuit is known. Therefore, the time required for the circuit to charge to its known voltage is calculated by the formula:

$$R_s = t/C$$

wherein $R_s$ is the resistance of the sensor, C is the capacitance of the detector circuitry and t is time.

The detector of the present invention measures the time it takes for the circuit to charge versus the amount of resistance in the circuit. A time measurement for a sensor to charge is a much better and more accurate measurement than a resistance measurement of a sensor for detecting the presence of carbon monoxide. The detector of the present invention measures the time required for the circuit to charge with a gated time measuring device, such as a microprocessor. Microprocessors measure time to a high degree of accuracy. By accurately measuring the time required for a sensor to charge, the variation in resistance values for sensors is eliminated. In essence, the detector of the present invention normalizes the resistance variability of the carbon monoxide sensor.

A detector, such as that of the present invention, which measures time versus resistance is a more accurate unit, can be auto-calibrated, requires fewer manufacturing steps and has a smaller margin of error in carbon monoxide detection. For the detector of the present invention, using a resistor-capacitor circuit to measure time versus a circuit which measures resistance, eliminates the need for a potentiometer as required by the prior art detectors, with all the inaccuracies inherent therein.

The detector of the present invention does not determine an absolute value for the carbon monoxide concentration in an air sample, but rather determines a threshold value of carbon monoxide concentration in an air sample which may have a detrimental affect on humans. This carbon monoxide concentration is about 100 parts per million (ppm). By measuring a threshold carbon monoxide concentration, transient events of exposure of the detector to hydrocarbons which could trigger the alarm, such as hairspray, ammonia, butane, etc., are eliminated, because the detector of the present invention can factor out, as non-alarm events, such one time occurrences.

The resistor-capacitor circuit of the detector of the present invention can be used for any type of carbon monoxide sensor or other toxic gas sensor which has a change in resistance value upon exposure to the toxic gas to be detected. A tin dioxide sensor, such as the Figaro sensor, or any other sensor which can detect the presence of carbon monoxide in an air sample, such as a copper manganese oxide sensor or any other suitable sensor, may be used in the detector of the present invention. The tin dioxide sensor is preferred, because of its ready availability. As would be obvious to one of ordinary skill in the art, the sensor of the detector of the present invention can be readily substituted with any other sensor specific for detection of some other toxic gas to detect such gas.

An additional disadvantage of the tin dioxide or Figaro sensor when used in a resistance measurement circuitry, is that the sensor requires conditioning time. The sensor must be run at a high current level for a variant length of time, which is specific to the subject sensor, to burn any contaminants off the sensor filament. This is another required step which adds to the cost of manufacture of the prior art detectors. In contrast, the detector of the present invention is auto-calibrated, as previously mentioned, by permanently affixing a resistance value for the sensor. Therefore, one less manufacturing step is required for the detector of the present invention and there is no need to sort sensors by resistance value prior to installation within the detector circuitry, both of which reduce the manufacturing cost of the detector of the present invention.

The detector of the present invention is more accurately calibrated than the prior art detectors. The calibration of the detector of the present invention is done by a gated time measuring device, preferably, a microprocessor in the detector instead of by hand with its attendant inaccuracies.

The microprocessor is used to calibrate the resistance value of the sensor at the point of manufacture of the detector of the present invention and the sensor cannot be recalibrated thereafter. In contrast, the prior art detectors could easily have the sensors recalibrated either inadvertently or intentionally by the potentiometer screw being loosened or tightened either manually or by jostling of the screw during transport, handling, installation, etc. of the detector.

To calibrate the sensor of the detector of the present invention, an average of two time measurement readings for the sensor to charge at a known carbon monoxide concentration is used, preferably 100 ppm, a threshold danger concentration of carbon monoxide. From this average time measurement, the resistance of the sensor is calculated and permanently burned into the sensor.

The standard air sampling interval rate of a carbon monoxide detector for a carbon monoxide concentration is about every two and one half minutes. The detector of the present invention can be set to other sampling interval rates which are greater than about or less than about two and one half minutes. For the detector of the present invention, the standard of about every two and one half minutes air sampling rate is preferred, because that is the current standard sampling rate specification as established by UL; however, the sampling rate of the detector of the present invention can be adjusted to comply with whatever sampling rate specifications are put into effect by UL.

For an air sample cycle of the detector of the present invention, the detector goes through the process steps shown in the microprocessor logic flowsheets shown in FIGS. 3, 4A, 4B and 4C. First, the sensor is heated with current to burn off any contaminants on the sensor (See FIG. 4A). The circuitry runs for about 60 seconds at high voltage, then for about 90 seconds at low voltage, after which time the circuitry is turned off for about two milliseconds to allow the sensor to sample the air. Next, a time measurement for the detector circuitry to charge is taken and the cycle is repeated.

Figure 4A:
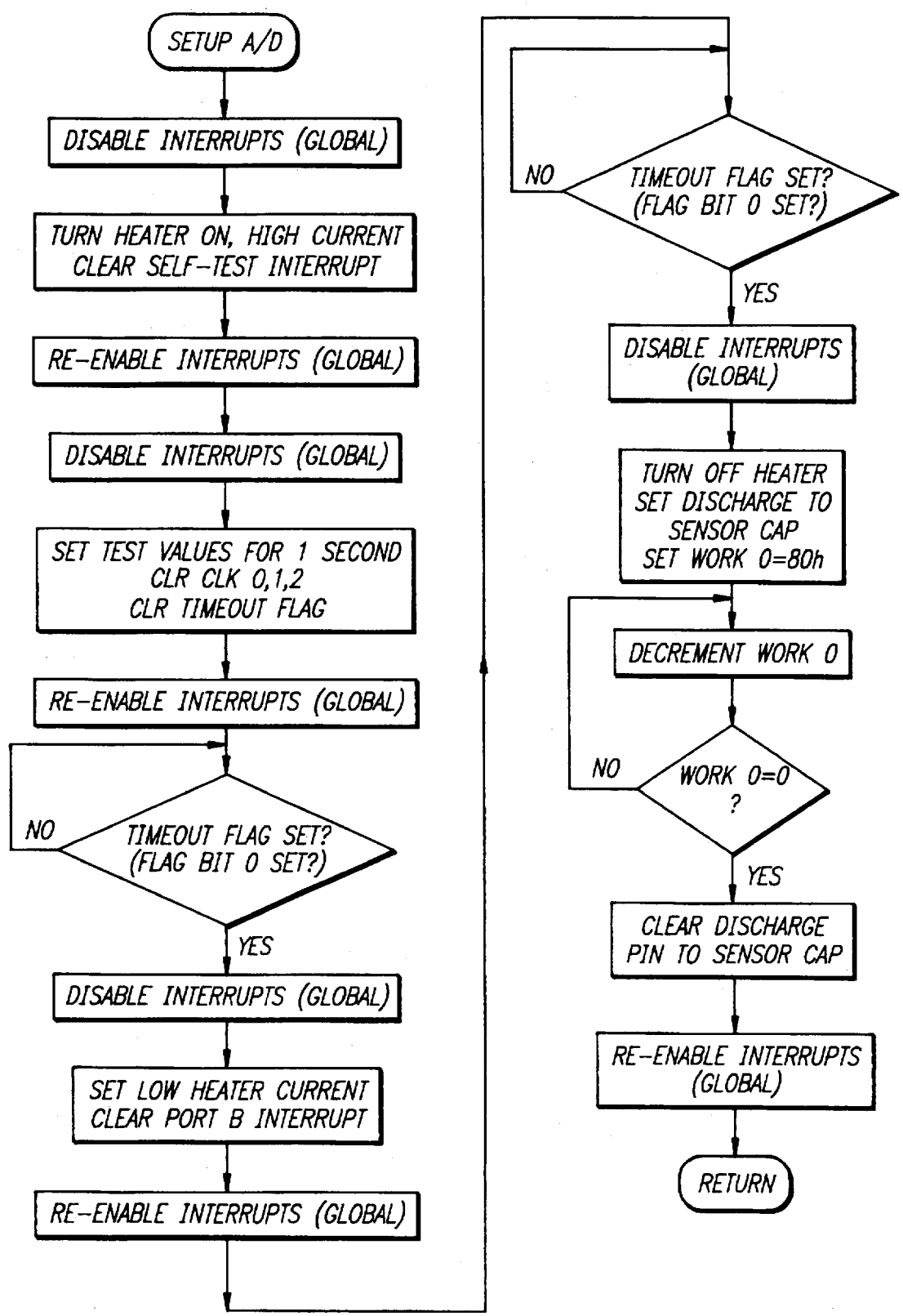
FIGS. 4A, 4B, 4C are flowcharts of the subroutines of the firmware of the detector of the present invention, including the initial set up test cycle of the detector, the polling test cycle of the detector and the testing result comparison cycle of the detector, respectively.
Figure 4B:
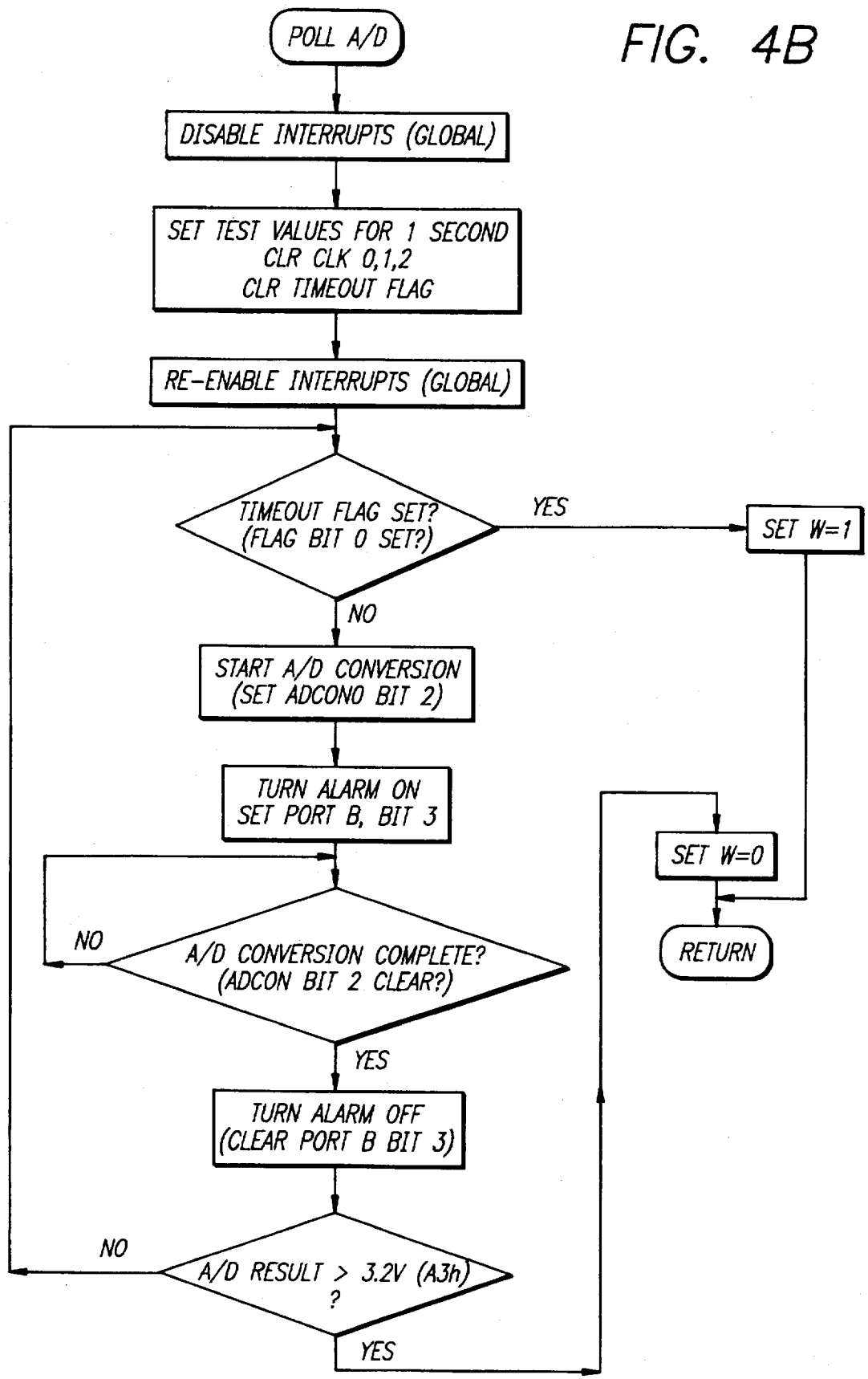
Figure 4C:
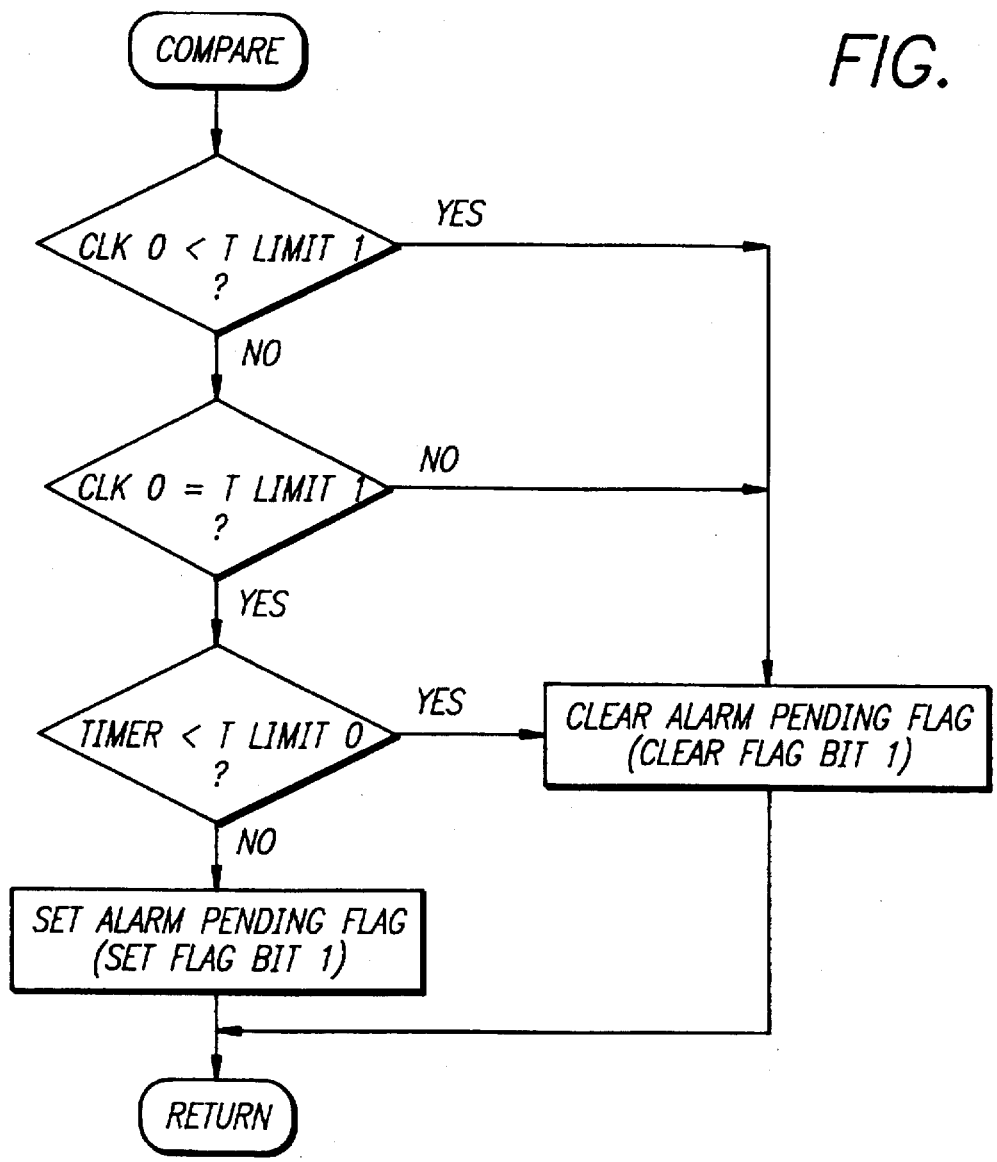

If the carbon monoxide concentration exceeds a pre-programmed threshold value in the microprocessor, then a first sample reading "yes" response is registered in the microprocessor (See FIG. 4B). A preferred threshold carbon monoxide concentration value is about 100 ppm. If a second sample reading of a threshold carbon monoxide concentration is detected, then the microprocessor registers two "yes" responses. If a third sample reading of a threshold carbon monoxide concentration is detected, then the microprocessor registers three "yes" responses. Finally, if a fourth sample reading of a threshold carbon monoxide concentration is detected, then the alarm of the detector of the present invention is triggered. If at any time during the four sample readings the microprocessor registers a "no" response, that is the threshold carbon monoxide concentration has not been detected, then the microprocessor resets itself, subtracts the "no" response from the pre-alarm state count and begins the sample reading cycle over (See FIG. 4C).

Four "yes" responses or alarm states must register in the microprocessor memory in order for the detector alarm to be triggered. For each of the alarm states, the detector flashes the count of the alarm state via a light emitting diode (LED) display—one flash for one alarm state, two flashes for two alarm states, three flashes for three alarm states and four flashes for four alarm states. At the fourth alarm state the detector flashes its LED display four times for a visual signal and emits an audio alarm signal. Therefore, at a dangerous carbon monoxide level the detector would alarm and alert a user after about ten minutes, which allows the user ample time to vacate the contaminated premises and remove himself from harm's way.

The multiple air sample readings taken by the detector allow the microprocessor to recognize and eliminate transient, short term events which might otherwise falsely trigger the detector alarm, such as exposure of the sensor to hydrocarbons, such as hairspray, ammonia, butane, and other such commonplace non-lethal residential, automobile and work place compounds. In addition, the microprocessor of the detector of the present invention is able to be programmed so that the detector alarm will be immediately triggered if the time measurement for the detector circuitry to charge meets or exceeds a dangerous or lethal carbon monoxide concentration level. The microprocessor can also be custom programmed to trigger the detector alarm at any other predetermined level of carbon monoxide concentration deemed to be hazardous.

Carbon monoxide concentration build up is cumulative in human beings, because humans do not flush carbon monoxide that they are exposed to out of their vascular systems. Therefore, long term, low level exposure to carbon monoxide is just as dangerous as short term, high level exposure to carbon monoxide. Accordingly, it is important to have a detector, such as that of the present invention, which can calculate a time weighted average for exposure to carbon monoxide concentrations in an air sample and, thereby, detect both high and low level harmful carbon monoxide concentrations.

Figure 1A:
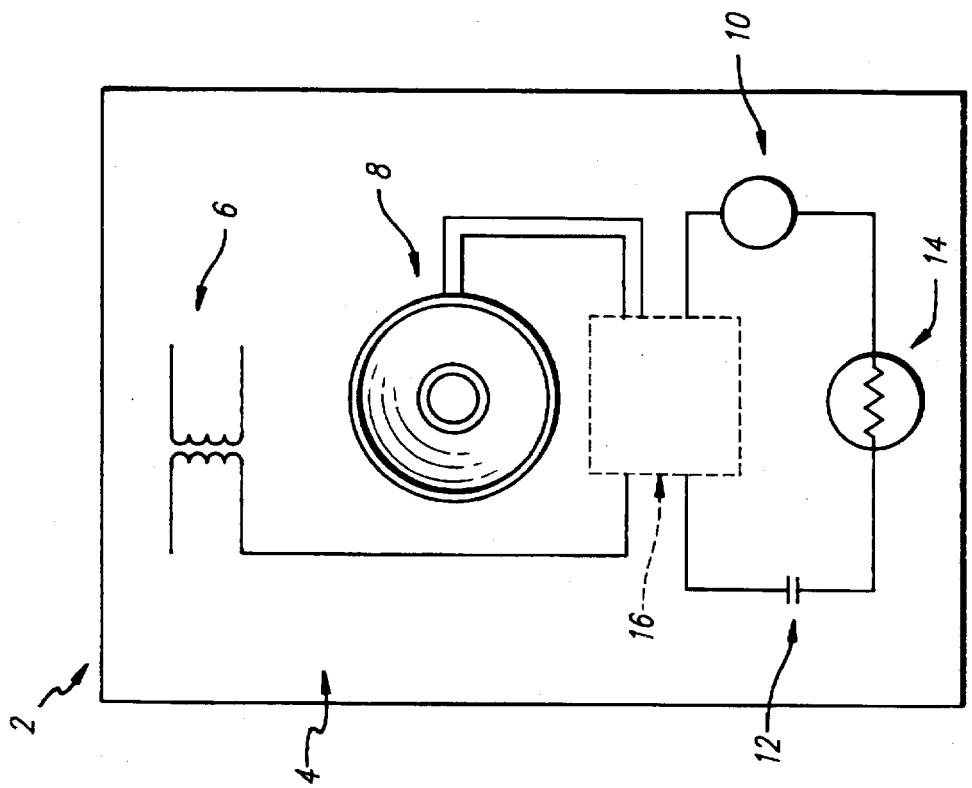

Front and back plan views of the firmware of the detector of the present invention are shown in FIGS. 1A and 1B, respectively. In FIG. 1A, a front plan view of the firmware of the detector 2 is comprised of a circuit board 4 upon which sets a transformer 6 which is integral with the circuit board 4 for converting common household voltage to from about 5 volts to about 12 volts, which is all the current needed to operate the detector 2 of the present invention. Also setting upon the circuit board 4 and integral therewith is a sensor 10 which is connected in series with a capacitor 12, which also sets upon and is integral with circuit board 4. Additionally, there is a thermistor 14 which sets upon and is integral with circuit board 4 and which compensates for any temperature or humidity changes in the ambient environment in which the detector is placed. The thermistor 14 is a critical feature of the detector 2 of the present invention, because its ability to compensate for air temperature and humidity changes enables the detector 2 to take accurate carbon monoxide concentration readings without having the sensor 10 impaired by temperature and humidity surges or extremes. The audio alarm 8 is also set upon and integral with the circuit board 4. The audio alarm 8 is triggered when the detector 2 detects a harmful carbon monoxide concentration.

FIG. 1B is a back plan view of the detector 2 of the present invention. Integral with the circuit board 4 is a microprocessor 16 and a non-volatile, permanent memory chip 18, commonly known as an EEProm. The EEProm 18 has a permanent memory which means that the electronic information stored in the chip will remain undisturbed whether the power supply to the detector 2 is on or off. Additionally, the memory of the EEProm 18 cannot be erased. The calibration data for the detector 2 is stored in the EEProm 18. The back side of the circuit board 4 is open to the audio alarm 8. The back side of the circuit board 4 also has a visual alarm 5, preferably an LED, which will be triggered when the detector 2 detects a harmful carbon monoxide concentration, as well as when the detector 2 reaches each alarm state prior to and leading up to the harmful carbon monoxide concentration detection state. The back side of the circuit board 4 also has a visual power indicator 7 to indicate whether the detector 2 is on or off.

The detector of the present invention has several other advantages over the prior art detectors. The detector performs an on-going systems check to detect any fault condition of the detector. For instance, the detector can detect if the sensor filament is open or disconnected. If the filament is open, or any other fault condition has occurred, then the microprocessor of the detector will trigger the detector alarm and alert the user to the detector malfunction.

The detector of the present invention is also a "green", or environmentally friendly, device, in that it runs in a low power mode until it detects the presence of carbon monoxide in an air sample. Upon such detection, it alerts a user when the carbon monoxide concentration is greater than or equal to about 100 parts per million (ppm). When this threshold concentration is reached, the detector alerts the user by flashing an LED visual alarm and an audio alarm as previously discussed.

The detector of the present invention is also physically smaller in size than the prior art detectors. Therefore, the detector of the present invention is more aesthetically appealing to a user and is easier to install for the user.

The casing of the detector of the present invention may be of any suitable, durable material, such as metal or high impact plastic. High impact plastic is the preferred casing material in order for the detector to comply with future, anticipated UL specifications for carbon monoxide detectors which state that the detector casing shall be of a non-metallic material. Additionally, the casing of the detector may be of any suitable, practical shape and dimensions, whether dictated by the detector firmware or not.

The smaller physical size of the detector of the present invention also makes it easier and less expensive to manufacture due to lower material costs. Another factor which contributes to the detector's lower manufacture costs is that it has fewer components, such as not requiring a potentiometer, than the prior art detectors and also requires minimal, if any, manual labor, such as the calibration of the potentiometer, thus saving on material and labor costs, respectively.

The detector of the present invention is also more reliable in that it rejects false alarms much better than do the prior art detectors. The false alarm rejection ability of the detector is due to several factors. First, the human error of the manual calibration of the sensor and potentiometer in the prior art detectors is eliminated by the auto-calibration of the detector of the present invention as previously discussed. Second, the transient events which can trigger a false alarm in the prior art detectors, such as a non-carbon monoxide hydrocarbon exposure as previously discussed, are screened out by the detector of the present invention, because it does multiple air sample readings, also as previously discussed.

For a power source, the detector of the present invention may be either a plug-in unit or a hard-wired unit. It may also be hooked to an off-site alarm with a response unit, such as a local fire station or private security entity. The detector may also have a battery back-up. With a standard 9 volt "transistor-type" battery, the detector will be able to operate on the battery power source for about 40 minutes before the battery is exhausted. However, even without the battery back-up, as previously discussed the detector's permanent EEProm memory will not be disturbed, thus, enabling the detector to resume normal functioning without interruption or misinformation once the power is restored to the detector.

Another important feature of the detector of the present invention is its ability to reset itself. The detector has a manual reset button. After the detector has alarmed and the reset button has been operated, then the detector has the ability to reset itself.

The prior art detectors are not able to be reset in a timely or practical fashion. For example, a prior art detector such as that disclosed in U.S. Pat. No. 5,280,273 uses a biomimetric gel sensor to detect the presence of carbon monoxide. In the presence of carbon monoxide the gel physically changes. Once the sensor has been exposed to carbon monoxide, the sensor requires over 48 hours at a temperature greater than 40° F. for the gel sensor to reset. In contrast to such prior art detectors, after it has been exposed to carbon monoxide, the detector of the present invention quickly resets itself after its reset button is operated. Additionally, the reset button of the detector of the present invention can be used to perform a system check of the detector to ensure it is functioning properly.

The detector of the present invention meets or exceeds all of the current UL specifications for carbon monoxide detectors. However, these specifications are currently being revised. Effective Oct. 1, 1995, the UL specifications will require, among other requirements, that all carbon monoxide detectors be able to be reset after exposure to carbon monoxide. As previously discussed, the detector of the present invention already meets and exceeds this particular UL specification requirement.

Other UL specification requirements pending revision include: (1) a visual and an audible alarm signal to indicate the presence of low concentrations of carbon monoxide gas over an extended period of time and/or high concentrations of gas over a short period of time; (2) the ability to detect a carbon monoxide concentration of 100±5 ppm within 16 minutes; (3) the detector shall not actuate an alarm at a carbon monoxide concentration of 80±3 ppm; (4) carbon monoxide detectors must have a manually operated reset button which enables the detector to reset itself and rearm its alarm within six minutes from the time the reset button is operated; and (5) the detector shall not actuate false alarms due to extreme high or low temperatures of above about 150° F. or below about −40° F., respectively, nor due to humidity of about 93% at about 142° F. As previously discussed in greater detail, the detector of the present invention not only meets or exceeds current UL specifications for carbon monoxide detectors, but also will meet or exceed the future, anticipated specifications to be effective Oct. 1, 1995.

The embodiments illustrated and discussed in the specification are intended only as exemplary and the many other feasible embodiments within the scope of this invention will be readily understood and appreciated by those having ordinary skill in the art. Nothing in the specification should be construed as limiting the scope of the present invention. Many changes may be made by those having ordinary skill in the art to produce a highly effective article of manufacture for a toxic gas detector without departing from the present invention. Accordingly, the present invention should be limited only by the claims.

We claim:

1. A gas detector comprising the elements of:
    a. a gas sensor;
    b. a capacitor;
    c. a transformer;
    d. a gated time measuring device; and
    e. a permanent memory chip;
all of which are interconnected by means of and are integral with a circuit board wherein the gated time measuring device measures a time for the capacitor to charge, which time measurement value is an indicator of the presence of a gas.

2. A detector as claimed in claim 1 further comprising an audio alarm.

3. A detector as claimed in claim 1 further comprising a visual alarm.

4. A detector as claimed in claim 1 further comprising a casing for housing the detector elements.

5. A detector as claimed in claim 1 wherein the capacitor and sensor are in a series circuit with each other.

6. A detector as claimed in claim 1 wherein the gated time measuring device is a microprocessor.

7. A detector as claimed in claim 1 wherein the detector may be reset.

8. A detector as claimed in claim 6 wherein the microprocessor will register an alarm state if a gas concentration in an air sample is greater than or equal to about a pre-determined concentration.

9. A detector as claimed in claim 8 wherein the microprocessor will trigger and flash a visual alarm for each alarm state.

10. A detector as claimed in claim 9 wherein the microprocessor will trigger an audio alarm upon four consecutive alarm state registrations.

11. A detector as claimed in claim 6 wherein the microprocessor will trigger an audio alarm and a visual alarm upon detection of a pre-determined gas concentration in an air sample.

12. A detector as claimed in claim 6 wherein the microprocessor makes a time measurement about every two and one half minutes.

13. A detector as claimed in claim 6 wherein the gas is carbon monoxide.

14. A detector as claimed in claim 13 wherein the sensor is selected from the group consisting of a tin dioxide sensor and a copper manganese dioxide sensor.

15. A detector as claimed in claim 14 wherein the microprocessor screens out transient hydrocarbon exposure events to the sensor.

16. A carbon monoxide detector comprising the elements of:
    a. a toxic gas sensor;
    b. a capacitor;
    c. a transformer;
    d. a gated measuring device;
    e. a permanent memory chip;
    f. an audio alarm;
    g. a visual alarm; and
    h. a power source
all of which are interconnected by means of and are integral with a circuit board, wherein all of the elements are housed in a casing, wherein the capacitor and the sensor are in a series circuit with each other and wherein the gated time measuring device measures a time for the capacitor to charge, which time measurement value is an indicator of the presence of carbon monoxide.

17. A detector as claimed in claim 16 wherein the gated time measuring device is a microprocessor.

18. A detector as claimed in claim 17 wherein the sensor is selected from the group consisting of a tin dioxide sensor and a copper manganese dioxide sensor.

19. A detector as claimed in claim 16 wherein the detector may be reset.

20. A detector as claimed in claim 17 wherein the microprocessor will register an alarm state if a carbon monoxide concentration in an air sample is greater than or equal to about 100 ppm.

21. A detector as claimed in claim 20 wherein the microprocessor will trigger and flash a visual alarm for each alarm state.

22. A detector as claimed in claim 21 wherein the microprocessor will trigger an audio alarm upon four consecutive alarm state registrations.

23. A detector as claimed in claim 17 wherein the microprocessor will trigger an audio alarm and a visual alarm upon detection of a lethal carbon monoxide concentration in an air sample.

24. A detector as claimed in claim 17 wherein the microprocessor makes a time measurement about every two and one half minutes.

25. A detector as claimed in claim 17 wherein the microprocessor screens out transient hydrocarbon exposure events to the sensor.

26. A detector as claimed in claim 16 further comprising a thermistor wherein the thermistor compensates for air temperature and humidity changes in an environment in which the detector is located.

* * * * *